(12) United States Patent
Govari et al.

(10) Patent No.: US 12,295,720 B2
(45) Date of Patent: *May 13, 2025

(54) VISUAL GUIDANCE FOR POSITIONING A DISTAL END OF A MEDICAL PROBE

(71) Applicant: Biosense Webster (Israel) Ltd., Yokneam (IL)

(72) Inventors: Assaf Govari, Haifa (IL); Vadim Gliner, Haifa (IL); Andres Claudio Altmann, Haifa (IL)

(73) Assignee: Biosense Webster (Israel) Ltd, Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/851,196

(22) Filed: Jun. 28, 2022

(65) Prior Publication Data

US 2023/0055089 A1    Feb. 23, 2023

Related U.S. Application Data

(63) Continuation of application No. 16/896,099, filed on Jun. 8, 2020, now Pat. No. 11,712,172.

(Continued)

(51) Int. Cl.
*A61B 5/06* (2006.01)
*A61B 5/00* (2006.01)
(Continued)

(52) U.S. Cl.
CPC .............. *A61B 5/066* (2013.01); *A61B 5/287* (2021.01); *A61B 5/343* (2021.01); *A61B 5/349* (2021.01);
(Continued)

(58) Field of Classification Search
CPC ......... A61B 5/066; A61B 5/349; A61B 5/367; A61B 5/343; A61B 5/287; A61B 5/6853; A61B 5/6858
See application file for complete search history.

(56) References Cited

U.S. PATENT DOCUMENTS 4,699,147 A   10/1987   Chilson et al.
4,940,064 A    7/1990   Desai
(Continued)

FOREIGN PATENT DOCUMENTS

CN   101247766 A   8/2008
CN   101292870 A   8/2008
(Continued)

OTHER PUBLICATIONS

Extended European Search Report issued in Application No. EP 20186466.7; dated Oct. 1, 2020; 8 pages.
(Continued)

*Primary Examiner* — Catherine M Voorhees
*Assistant Examiner* — Roland Dinga

(57) ABSTRACT

A method, including receiving, from electrodes positioned within a heart, first signals from at least three of the electrodes indicating electrical activity in tissue with which the at least three of the electrodes engage, and second signals indicating locations of the at least three electrodes. The second signals are processed to compute the locations of the at least three electrodes and to determine a geometric center of the locations. Based on the signals, an electroanatomical map is generated for an area of the tissue including the geometric center, and an arrhythmia focus is determined in the map. A circle is presented, and within the circle, a region of the map is presented including the geometric center and the focus so that the geometric center on the map aligns with a center of the circle, the region within the circle indicating a spatial relationship between the geometric center and the focus.

19 Claims, 6 Drawing Sheets

Related U.S. Application Data

(60) Provisional application No. 62/875,770, filed on Jul. 18, 2019.

(51) Int. Cl.
  *A61B 5/287* (2021.01)
  *A61B 5/343* (2021.01)
  *A61B 5/349* (2021.01)
  *A61B 5/367* (2021.01)

(52) U.S. Cl.
  CPC ............ *A61B 5/367* (2021.01); *A61B 5/6853* (2013.01); *A61B 5/6858* (2013.01)

(56) References Cited

U.S. PATENT DOCUMENTS

| | | | |
|---|---|---|---|
| 5,215,103 A | 6/1993 | Desai | |
| 5,255,679 A | 10/1993 | Imran | |
| 5,293,869 A | 3/1994 | Edwards et al. | |
| 5,309,910 A | 5/1994 | Edwards et al. | |
| 5,313,943 A | 5/1994 | Houser et al. | |
| 5,324,284 A | 6/1994 | Imran | |
| 5,345,936 A | 9/1994 | Pomeranz et al. | |
| 5,365,926 A | 11/1994 | Desai | |
| 5,391,199 A | 2/1995 | Ben-Haim | |
| 5,396,887 A | 3/1995 | Imran | |
| 5,400,783 A | 3/1995 | Pomeranz et al. | |
| 5,411,025 A | 5/1995 | Webster, Jr. | |
| 5,415,166 A | 5/1995 | Imran | |
| 5,443,489 A | 8/1995 | Ben-Haim | |
| 5,456,254 A | 10/1995 | Pietroski et al. | |
| 5,465,717 A | 11/1995 | Imran et al. | |
| 5,476,495 A | 12/1995 | Kordis et al. | |
| 5,499,981 A | 3/1996 | Kordis | |
| 5,526,810 A | 6/1996 | Wang | |
| 5,546,940 A | 8/1996 | Panescu et al. | |
| 5,549,108 A | 8/1996 | Edwards et al. | |
| 5,558,073 A | 9/1996 | Pomeranz et al. | |
| 5,558,091 A | 9/1996 | Acker et al. | |
| 5,577,509 A | 11/1996 | Panescu et al. | |
| 5,595,183 A | 1/1997 | Swanson et al. | |
| 5,598,848 A | 2/1997 | Swanson et al. | |
| 5,609,157 A | 3/1997 | Panescu et al. | |
| 5,628,313 A | 5/1997 | Webster, Jr. | |
| 5,657,755 A * | 8/1997 | Desai ................... | A61B 5/287 606/41 |
| 5,681,280 A | 10/1997 | Rusk et al. | |
| 5,722,401 A | 3/1998 | Pietroski et al. | |
| 5,722,402 A | 3/1998 | Swanson et al. | |
| 5,722,403 A | 3/1998 | McGee et al. | |
| 5,725,525 A | 3/1998 | Kordis | |
| 5,730,128 A | 3/1998 | Pomeranz et al. | |
| 5,772,590 A | 6/1998 | Webster, Jr. | |
| 5,782,899 A | 7/1998 | Imran | |
| 5,823,189 A | 10/1998 | Kordis | |
| 5,881,727 A | 3/1999 | Edwards | |
| 5,893,847 A | 4/1999 | Kordis | |
| 5,904,680 A | 5/1999 | Kordis et al. | |
| 5,911,739 A | 6/1999 | Kordis et al. | |
| 5,928,228 A | 7/1999 | Kordis et al. | |
| 5,944,022 A | 8/1999 | Nardella et al. | |
| 5,968,040 A | 10/1999 | Swanson et al. | |
| 5,983,126 A | 11/1999 | Wittkampf | |
| 6,014,579 A | 1/2000 | Pomeranz et al. | |
| 6,014,590 A | 1/2000 | Whayne et al. | |
| 6,119,030 A | 9/2000 | Morency | |
| 6,172,499 B1 | 1/2001 | Ashe | |
| 6,216,043 B1 | 4/2001 | Swanson et al. | |
| 6,216,044 B1 | 4/2001 | Kordis | |
| 6,239,724 B1 | 5/2001 | Doron et al. | |
| 6,332,089 B1 | 12/2001 | Acker et al. | |
| 6,428,537 B1 | 8/2002 | Swanson et al. | |
| 6,456,864 B1 | 9/2002 | Swanson et al. | |
| 6,484,118 B1 | 11/2002 | Govari | |
| 6,574,492 B1 | 6/2003 | Ben-Haim et al. | |
| 6,584,345 B2 | 6/2003 | Govari | |
| 6,600,948 B2 | 7/2003 | Ben-Haim et al. | |
| 6,618,612 B1 | 9/2003 | Acker et al. | |
| 6,690,963 B2 | 2/2004 | Ben-Haim et al. | |
| 6,738,655 B1 | 5/2004 | Sen et al. | |
| 6,741,878 B2 | 5/2004 | Fuimaono et al. | |
| 6,748,255 B2 | 6/2004 | Fuimaono et al. | |
| 6,780,183 B2 | 8/2004 | Jimenez, Jr. et al. | |
| 6,788,967 B2 | 9/2004 | Ben-Haim et al. | |
| 6,837,886 B2 | 1/2005 | Collins et al. | |
| 6,866,662 B2 | 3/2005 | Fuimaono et al. | |
| 6,892,091 B1 | 5/2005 | Ben-Haim et al. | |
| 6,970,730 B2 | 11/2005 | Fuimaono et al. | |
| 6,973,340 B2 | 12/2005 | Fuimaono et al. | |
| 6,980,858 B2 | 12/2005 | Fuimaono et al. | |
| 7,048,734 B1 | 5/2006 | Fleischman et al. | |
| 7,149,563 B2 | 12/2006 | Fuimaono et al. | |
| 7,255,695 B2 | 8/2007 | Falwell et al. | |
| 7,257,434 B2 | 8/2007 | Fuimaono et al. | |
| 7,399,299 B2 | 7/2008 | Daniel et al. | |
| 7,410,486 B2 | 8/2008 | Fuimaono et al. | |
| 7,522,950 B2 | 4/2009 | Fuimaono et al. | |
| 7,536,218 B2 | 5/2009 | Govari et al. | |
| RE41,334 E | 5/2010 | Beatty et al. | |
| 7,756,576 B2 | 7/2010 | Levin | |
| 7,846,157 B2 | 12/2010 | Kozel | |
| 7,848,787 B2 | 12/2010 | Osadchy | |
| 7,869,865 B2 | 1/2011 | Govari et al. | |
| 7,907,994 B2 * | 3/2011 | Stolarski ................. | A61B 5/35 600/515 |
| 7,930,018 B2 | 4/2011 | Harlev et al. | |
| 8,007,495 B2 | 8/2011 | McDaniel et al. | |
| 8,048,063 B2 | 11/2011 | Aeby et al. | |
| 8,103,327 B2 | 1/2012 | Harlev et al. | |
| 8,167,845 B2 | 5/2012 | Wang et al. | |
| 8,224,416 B2 | 7/2012 | De La Rama et al. | |
| 8,224,432 B2 | 7/2012 | MacAdam et al. | |
| 8,235,988 B2 | 8/2012 | Davis et al. | |
| 8,326,419 B2 | 12/2012 | Rosenberg et al. | |
| 8,346,339 B2 | 1/2013 | Kordis et al. | |
| 8,435,232 B2 | 5/2013 | Aeby et al. | |
| 8,447,377 B2 | 5/2013 | Harlev et al. | |
| 8,456,182 B2 | 6/2013 | Bar-Tal et al. | |
| 8,498,686 B2 | 7/2013 | Grunewald | |
| 8,517,999 B2 | 8/2013 | Pappone et al. | |
| 8,545,490 B2 | 10/2013 | Mihajlovic et al. | |
| 8,560,086 B2 | 10/2013 | Just et al. | |
| 8,567,265 B2 | 10/2013 | Aeby et al. | |
| 8,577,450 B1 | 11/2013 | Chmiel et al. | |
| 8,712,550 B2 | 4/2014 | Grunewald | |
| 8,755,861 B2 | 6/2014 | Harlev et al. | |
| 8,825,130 B2 | 9/2014 | Just et al. | |
| 8,906,011 B2 | 12/2014 | Gelbart et al. | |
| 8,945,120 B2 | 2/2015 | McDaniel et al. | |
| 8,979,839 B2 | 3/2015 | De La Rama et al. | |
| 9,037,264 B2 | 5/2015 | Just et al. | |
| 9,131,980 B2 | 9/2015 | Bloom | |
| 9,204,929 B2 | 12/2015 | Solis | |
| 9,277,960 B2 | 3/2016 | Weinkam et al. | |
| 9,314,208 B1 | 4/2016 | Altmann et al. | |
| 9,339,331 B2 | 5/2016 | Tegg et al. | |
| 9,486,282 B2 | 11/2016 | Solis | |
| 9,554,718 B2 | 1/2017 | Bar-Tal et al. | |
| D782,686 S | 3/2017 | Werneth et al. | |
| 9,585,588 B2 | 3/2017 | Marecki et al. | |
| 9,597,036 B2 | 3/2017 | Aeby et al. | |
| 9,687,297 B2 | 6/2017 | Just et al. | |
| 9,693,733 B2 | 7/2017 | Altmann et al. | |
| 9,782,099 B2 | 10/2017 | Williams et al. | |
| 9,788,895 B2 | 10/2017 | Solis | |
| 9,801,681 B2 | 10/2017 | Laske et al. | |
| 9,814,618 B2 | 11/2017 | Nguyen et al. | |
| 9,833,161 B2 | 12/2017 | Govari | |
| 9,894,756 B2 | 2/2018 | Weinkam et al. | |
| 9,895,073 B2 | 2/2018 | Solis | |
| 9,907,609 B2 | 3/2018 | Cao et al. | |
| 9,974,460 B2 | 5/2018 | Wu et al. | |
| 9,986,949 B2 | 6/2018 | Govari et al. | |
| 9,993,160 B2 | 6/2018 | Salvestro et al. | |

(56) References Cited

U.S. PATENT DOCUMENTS

| | | |
|---|---|---|
| 10,014,607 B1 | 7/2018 | Govari et al. |
| 10,028,376 B2 | 7/2018 | Weinkam et al. |
| 10,034,637 B2 | 7/2018 | Harlev et al. |
| 10,039,494 B2 | 8/2018 | Altmann et al. |
| 10,045,707 B2 | 8/2018 | Govari |
| 10,078,713 B2 | 9/2018 | Auerbach et al. |
| 10,111,623 B2 | 10/2018 | Jung et al. |
| 10,130,420 B2 | 11/2018 | Basu et al. |
| 10,136,828 B2 | 11/2018 | Houben et al. |
| 10,143,394 B2 | 12/2018 | Solis |
| 10,172,536 B2 | 1/2019 | Maskara et al. |
| 10,182,762 B2 | 1/2019 | Just et al. |
| 10,194,818 B2 | 2/2019 | Williams et al. |
| 10,201,311 B2 | 2/2019 | Chou et al. |
| 10,219,860 B2 | 3/2019 | Harlev et al. |
| 10,219,861 B2 | 3/2019 | Just et al. |
| 10,231,328 B2 | 3/2019 | Weinkam et al. |
| 10,238,309 B2 | 3/2019 | Bar-Tal et al. |
| 10,278,590 B2 | 5/2019 | Salvestro et al. |
| D851,774 S | 6/2019 | Werneth et al. |
| 10,314,505 B2 | 6/2019 | Williams et al. |
| 10,314,507 B2 | 6/2019 | Govari et al. |
| 10,314,648 B2 | 6/2019 | Ge et al. |
| 10,314,649 B2 | 6/2019 | Bakos et al. |
| 10,349,855 B2 | 7/2019 | Zeidan et al. |
| 10,350,003 B2 | 7/2019 | Weinkam et al. |
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,857 B2 | 12/2019 | Guggenberger et al. |
| 10,542,620 B2 | 1/2020 | Weinkam et al. |
| 10,575,743 B2 | 3/2020 | Basu et al. |
| 10,575,745 B2 | 3/2020 | Solis |
| 10,582,871 B2 | 3/2020 | Williams et al. |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,867 B2 | 4/2020 | Viswanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 11,712,172 B2* | 8/2023 | Govari .............. A61B 5/6858 600/515 |
| 2003/0013958 A1* | 1/2003 | Govari .............. A61B 8/483 600/443 |
| 2004/0210121 A1 | 10/2004 | Fuimaono et al. |
| 2006/0009689 A1 | 1/2006 | Fuimaono et al. |
| 2006/0009690 A1 | 1/2006 | Fuimaono et al. |
| 2006/0100669 A1 | 5/2006 | Fuimaono et al. |
| 2007/0093806 A1 | 4/2007 | Desai et al. |
| 2007/0276212 A1 | 11/2007 | Fuimaono et al. |
| 2008/0188765 A1 | 8/2008 | Stolarski et al. |
| 2008/0234564 A1 | 9/2008 | Beatty et al. |
| 2011/0118726 A1 | 5/2011 | De La Rama et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0301597 A1 | 12/2011 | McDaniel et al. |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0184569 A1 | 7/2013 | Strommer et al. |
| 2013/0190587 A1 | 7/2013 | Lopes et al. |
| 2013/0274582 A1 | 10/2013 | Afonso et al. |
| 2013/0296852 A1 | 11/2013 | Madjarov et al. |
| 2014/0025069 A1 | 1/2014 | Willard et al. |
| 2014/0052118 A1 | 2/2014 | Laske et al. |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0257069 A1 | 9/2014 | Eliason et al. |
| 2014/0276712 A1 | 9/2014 | Mallin et al. |
| 2014/0303452 A1 | 10/2014 | Ghaffari |
| 2014/0309512 A1 | 10/2014 | Govari et al. |
| 2015/0011991 A1 | 1/2015 | Buysman et al. |
| 2015/0045863 A1 | 2/2015 | Litscher et al. |
| 2015/0080693 A1 | 3/2015 | Solis |
| 2015/0105770 A1 | 4/2015 | Amit |
| 2015/0119878 A1 | 4/2015 | Heisel et al. |
| 2015/0133919 A1 | 5/2015 | McDaniel et al. |
| 2015/0208942 A1 | 7/2015 | Bar-Tal et al. |
| 2015/0250424 A1 | 9/2015 | Govari et al. |
| 2015/0270634 A1 | 9/2015 | Buesseler et al. |
| 2015/0342532 A1 | 12/2015 | Basu et al. |
| 2016/0007852 A1* | 1/2016 | Warner .............. A61B 6/487 600/374 |
| 2016/0038047 A1* | 2/2016 | Urman .............. A61B 5/055 600/509 |
| 2016/0081746 A1 | 3/2016 | Solis |
| 2016/0113582 A1 | 4/2016 | Altmann et al. |
| 2016/0113709 A1 | 4/2016 | Maor |
| 2016/0183877 A1 | 6/2016 | Williams et al. |
| 2016/0228023 A1 | 8/2016 | Govari |
| 2016/0228062 A1 | 8/2016 | Altmann et al. |
| 2016/0278853 A1 | 9/2016 | Ogle et al. |
| 2016/0302858 A1 | 10/2016 | Bencini |
| 2016/0338770 A1 | 11/2016 | Bar-Tal et al. |
| 2017/0027638 A1 | 2/2017 | Solis |
| 2017/0065198 A1* | 3/2017 | Ruppersberg .......... A61B 5/341 |
| 2017/0065227 A1 | 3/2017 | Marrs et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0095173 A1 | 4/2017 | Bar-Tal et al. |
| 2017/0100187 A1 | 4/2017 | Basu et al. |
| 2017/0143227 A1 | 5/2017 | Marecki et al. |
| 2017/0156790 A1 | 6/2017 | Aujla |
| 2017/0172442 A1 | 6/2017 | Govari |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0265812 A1 | 9/2017 | Williams et al. |
| 2017/0281031 A1 | 10/2017 | Houben et al. |
| 2017/0281268 A1 | 10/2017 | Tran et al. |
| 2017/0296125 A1 | 10/2017 | Altmann et al. |

(56) References Cited

U.S. PATENT DOCUMENTS

| | | |
|---|---|---|
| 2017/0296251 A1 | 10/2017 | Wu et al. |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0008203 A1 | 1/2018 | Iyun et al. |
| 2018/0028084 A1 | 2/2018 | Williams et al. |
| 2018/0049803 A1 | 2/2018 | Solis |
| 2018/0085064 A1 | 3/2018 | Auerbach et al. |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168511 A1 | 6/2018 | Hall et al. |
| 2018/0184982 A1 | 7/2018 | Basu et al. |
| 2018/0192958 A1 | 7/2018 | Wu |
| 2018/0206792 A1 | 7/2018 | Auerbach et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0279954 A1 | 10/2018 | Hayam et al. |
| 2018/0296108 A1* | 10/2018 | Stewart .................. A61B 5/349 |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0325418 A1* | 11/2018 | Ghoraani ............... A61B 5/061 |
| 2018/0338722 A1 | 11/2018 | Altmann et al. |
| 2018/0344188 A1 | 12/2018 | Govari |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0076045 A1* | 3/2019 | Katz ...................... A61B 5/339 |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0155224 A1 | 5/2020 | Bar-Tal |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | Desimone et al. |
| 2020/0375689 A1* | 12/2020 | Govari ................... A61B 5/282 |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0161592 A1 | 6/2021 | Altmann et al. |
| 2021/0162210 A1 | 6/2021 | Altmann et al. |
| 2021/0169421 A1 | 6/2021 | Govari |
| 2021/0169550 A1 | 6/2021 | Govari et al. |
| 2021/0169567 A1 | 6/2021 | Govari et al. |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0177503 A1 | 6/2021 | Altmann et al. |
| 2021/0178166 A1 | 6/2021 | Govari et al. |
| 2021/0186363 A1 | 6/2021 | Gliner et al. |
| 2021/0186604 A1 | 6/2021 | Altmann et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |

FOREIGN PATENT DOCUMENTS

| | | |
|---|---|---|
| CN | 102625669 A | 8/2012 |
| CN | 103354730 A | 10/2013 |
| CN | 103565432 A | 2/2014 |
| CN | 104582614 A | 4/2015 |
| CN | 105992564 A | 10/2016 |
| CN | 109480821 A | 3/2019 |
| CN | 111248993 A | 6/2020 |
| CN | 111248996 A | 6/2020 |

(56) References Cited

FOREIGN PATENT DOCUMENTS

| | | | |
|---|---|---|---|
| CN | 112006672 | A | 12/2020 |
| EP | 0668740 | A1 | 8/1995 |
| EP | 0644738 | B1 | 3/2000 |
| EP | 0727183 | B1 | 11/2002 |
| EP | 0727184 | B1 | 12/2002 |
| EP | 2783651 | A1 | 10/2014 |
| EP | 2699151 | B1 | 11/2015 |
| EP | 2699152 | B1 | 11/2015 |
| EP | 2699153 | B1 | 12/2015 |
| EP | 2498706 | B1 | 4/2016 |
| EP | 2578173 | B1 | 6/2017 |
| EP | 3238645 | A1 | 11/2017 |
| EP | 2884931 | B1 | 1/2018 |
| EP | 2349440 | B1 | 8/2019 |
| EP | 3318211 | B1 | 12/2019 |
| EP | 3581135 | A1 | 12/2019 |
| EP | 2736434 | B1 | 2/2020 |
| EP | 3451962 | B1 | 3/2020 |
| EP | 3972510 | A1 | 3/2022 |
| JP | 20125293552 | A | 11/2012 |
| JP | 2014506171 | A | 3/2014 |
| JP | 2019051309 | A | 4/2019 |
| WO | 9421167 | A1 | 9/1994 |
| WO | 9421169 | A1 | 9/1994 |
| WO | 9625095 | A1 | 8/1996 |
| WO | 9634560 | A1 | 11/1996 |
| WO | 0182814 | A2 | 10/2004 |
| WO | 2004087249 | A2 | 10/2004 |
| WO | 2012100185 | A2 | 7/2012 |
| WO | 2013052852 | A1 | 4/2013 |
| WO | 2013162884 | A1 | 10/2013 |
| WO | 2013173917 | A1 | 11/2013 |
| WO | 2013176881 | A1 | 11/2013 |
| WO | 2014176205 | A1 | 10/2014 |
| WO | 2016019760 | A1 | 2/2016 |
| WO | 2016044687 | A1 | 3/2016 |
| WO | 2018111600 | A1 | 6/2018 |
| WO | 2018191149 | A1 | 10/2018 |
| WO | 2019084442 | A1 | 5/2019 |
| WO | 2019143960 | A1 | 7/2019 |
| WO | 2020026217 | A1 | 2/2020 |
| WO | 2020206328 | A1 | 10/2020 |

OTHER PUBLICATIONS

English translation of Search Report dated Mar. 22, 2024, from corresponding Japanese Application No. 2020-122716.
English translation of Notice of Reasons for Refusal dated Apr. 23, 2024, from corresponding Japanese Application No. 2020-122716.
English translation of Written Opinion dated Jul. 10, 2024, from corresponding Japanese Application No. 2020-122716.
Search Report dated Feb. 22, 2025, from corresponding Chinese Application No. CN202010691074.X.
First Office Action with English translation dated Feb. 22, 2025, from corresponding Chinese Application No. CN202010691074.X.

* cited by examiner

VISUAL GUIDANCE FOR POSITIONING A DISTAL END OF A MEDICAL PROBE

CROSS-REFERENCE TO RELATED APPLICATIONS

This application claims the benefit of U.S. patent application Ser. No. 16/896,099 filed 8 Jun. 2020 and U.S. Provisional Patent Application 62/875,770, filed Jul. 18, 2019, each of which is incorporated herein by reference.

FIELD OF THE INVENTION

The present invention relates generally to medical imaging, and specifically to providing visual feedback to aid in guiding a distal end of a medical probe to a location in a body cavity requiring medical treatment.

BACKGROUND OF THE INVENTION

Some medical procedures, such as mapping a cavity of a body organ (e.g., a heart), are performed by inserting a medical probe into the cavity. In some configurations, the medical probe comprises a distal segment that comprises multiple electrodes that can measure a physiological property such as a local surface electrical potential at a location in a heart.

Examples of medical probes comprising multiple electrodes include balloon catheters and basket catheters. In some configurations, these medical probes can deliver radio frequency (RF) current to ablate tissue in contact with the probe's distal end in order to provide a therapeutic result.

U.S. Pat. No. 8,577,450 to Chmiel et al. describes a graphic interface for multi-spine probe. The graphic interface includes a circle, the center of the circle representing a location of the distal end of the body of a catheter, and radii of the circle representing locations orientations of spines mounted at the distal end of the catheter.

U.S. Patent Application 2013/0274582 to Afonso et al. describes a method for diagnosing arrhythmias and directing catheter therapies. The method includes creating, for a catheter having a spiral-shaped distal comprising multiple electrodes, a representation of the catheter that may be superimposed on a map, model or image of the tissue.

U.S. Pat. No. 5,722,402 to Swanson et al. describes a method for guiding movable electrode elements within multiple-electrode structures. The method includes presenting, using different shades of color, a normalized distribution of voltages detected by electrodes of a basket catheter.

U.S. Patent Application 2013/0184569 to Strommer et al. describes a method for producing an electrophysiological map of a heart. The method includes generating a local activation time map of a heart by superimposing a representation of the position of a distal tip of a catheter on a marked image.

U.S. Pat. No. 8,224,432 to MacAdam et al. describes a method of rapid 3D mapping using multi-electrode position data. The method includes applying color coding to a map which depicts variations in activation time or any other parameter being mapped in accordance with a color scale.

U.S. Pat. No. 8,326,419 to Rosenberg et al. describes a method for therapy optimization via multi-dimensional mapping. The method includes generating an electromechanical delay map by subtracting local electrical activation times from corresponding local mechanical activation times, and rendering at least the electromechanical delay map to a display. The method may also include rendering an electromechanical delay map in color, where a color scale quantitatively identifies electromechanical delay values (e.g., via open or filled contours).

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The description above is presented as a general overview of related art in this field and should not be construed as an admission that any of the information it contains constitutes prior art against the present patent application.

SUMMARY OF THE INVENTION

There is provided, in accordance with an embodiment of the present invention a method, including receiving, from an intracardiac catheter, having a distal end including a plurality of electrodes, within a heart of a subject, first signals from at least three of the electrodes responsive to electrical activity in myocardial tissue with which the at least three of the electrodes are in contact, receiving second signals that are indicative of respective location coordinates of the at least three electrodes within the heart, processing the second signals so as to compute the respective location coordinates of the at least three electrodes and to determine a geometric center of the respective location coordinates, generating, based on the first signals and the second signals, an electroanatomical map for an area of the myocardial tissue including the determined geometric center, determining, in the map, a focus of an arrhythmia in the area of the myocardial tissue, presenting, on a display, a circle, and presenting, within the circle, a region of the map including the geometric center and the focus of the arrhythmia so that the geometric center on the map aligns with a center of the circle, wherein the region of the map presented within the circle indicates a spatial relationship between the geometric center and the focus of the arrhythmia.

In some embodiments, the electrical activity includes local activation time values. In additional embodiments, presenting the region of the map with the focus of the arrhythmia includes plotting the local activation time values against their respective locations.

In one embodiment, the arrhythmia includes a rotor having at least one focus. In another embodiment, the arrhythmia includes a focal.

In further embodiments, presenting the region of the map with the geometric center includes presenting, in the circle, an icon at a position corresponding to a location of the focus of the arrhythmia relative to the geometric center. In other embodiments, presenting the circle and the region of the map includes overlaying the circle on the electroanatomical map. In supplemental embodiments, the method also includes presenting, within the circle, a path of the arrhythmia from the focus of the arrhythmia.

In one embodiment, the intracardiac catheter includes a balloon catheter. In another embodiment, the intracardiac catheter includes a basket catheter.

In an additional embodiment, generating the electroanatomical map may include presenting the map on the display at a first resolution. In this additional embodiment, presenting the region may include presenting the region at a second resolution greater than the first resolution.

There is also provided, in accordance with an embodiment of the present invention an apparatus, including an intracardiac catheter configured to be inserted into a cardiac chamber, a plurality of electrodes affixed to a distal end of the intracardiac catheter, a display, and a processor configured to receive, from the intracardiac catheter inserted into a given cardiac chamber, first signals from at least three of the electrodes responsive to electrical activity in myocardial tissue with which the at least three of the electrodes are in contact, to receive second signals that are indicative of respective location coordinates of the at least three electrodes within the heart, to process the second signals so as to compute the respective location coordinates of the at least three electrodes and to determine a geometric center of the respective location coordinates, to generating, based on the first signals and the second signals, an electroanatomical map for an area of the myocardial tissue including the determined geometric center, to determine, in the map, a focus of an arrhythmia in the area of the myocardial tissue, to present, on the display, a circle; and to present, within the circle, a region of the map including the geometric center and the focus of the arrhythmia so that the geometric center on the map aligns with a center of the circle, wherein the region of the map presented within the circle indicates a spatial relationship between the geometric center and the focus of the arrhythmia.

There is further provided, in accordance with an embodiment of the present invention a computer software product, operated in conjunction with a intracardiac catheter having a distal end including a plurality of electrodes, the product including a non-transitory computer-readable medium, in which program instructions are stored, which instructions, when read by a computer, cause the computer to receive, from the intracardiac catheter positioned within a heart of a subject, first signals from at least three of the electrodes responsive to electrical activity in myocardial tissue with which the at least three of the electrodes are in contact, to receive second signals that are indicative of respective location coordinates of the at least three electrodes within the heart, to process the second signals so as to compute the respective location coordinates of the at least three electrodes and to determine a geometric center of the respective location coordinates, to generate, based on the first signals and the second signals, an electroanatomical map for an area of the myocardial tissue including the determined geometric center, to determine, in the map, a focus of an arrhythmia in the area of the myocardial tissue, to present, on a display, a circle, and to present, within the circle, a region of the map including the geometric center and the focus of the arrhythmia so that the geometric center on the map aligns with a center of the circle, wherein the region of the map presented within the circle indicates a spatial relationship between the geometric center and the focus of the arrhythmia.

BRIEF DESCRIPTION OF THE DRAWINGS

The disclosure is herein described, by way of example only, with reference to the accompanying drawings, wherein.

DETAILED DESCRIPTION OF EMBODIMENTS

Figure 1:
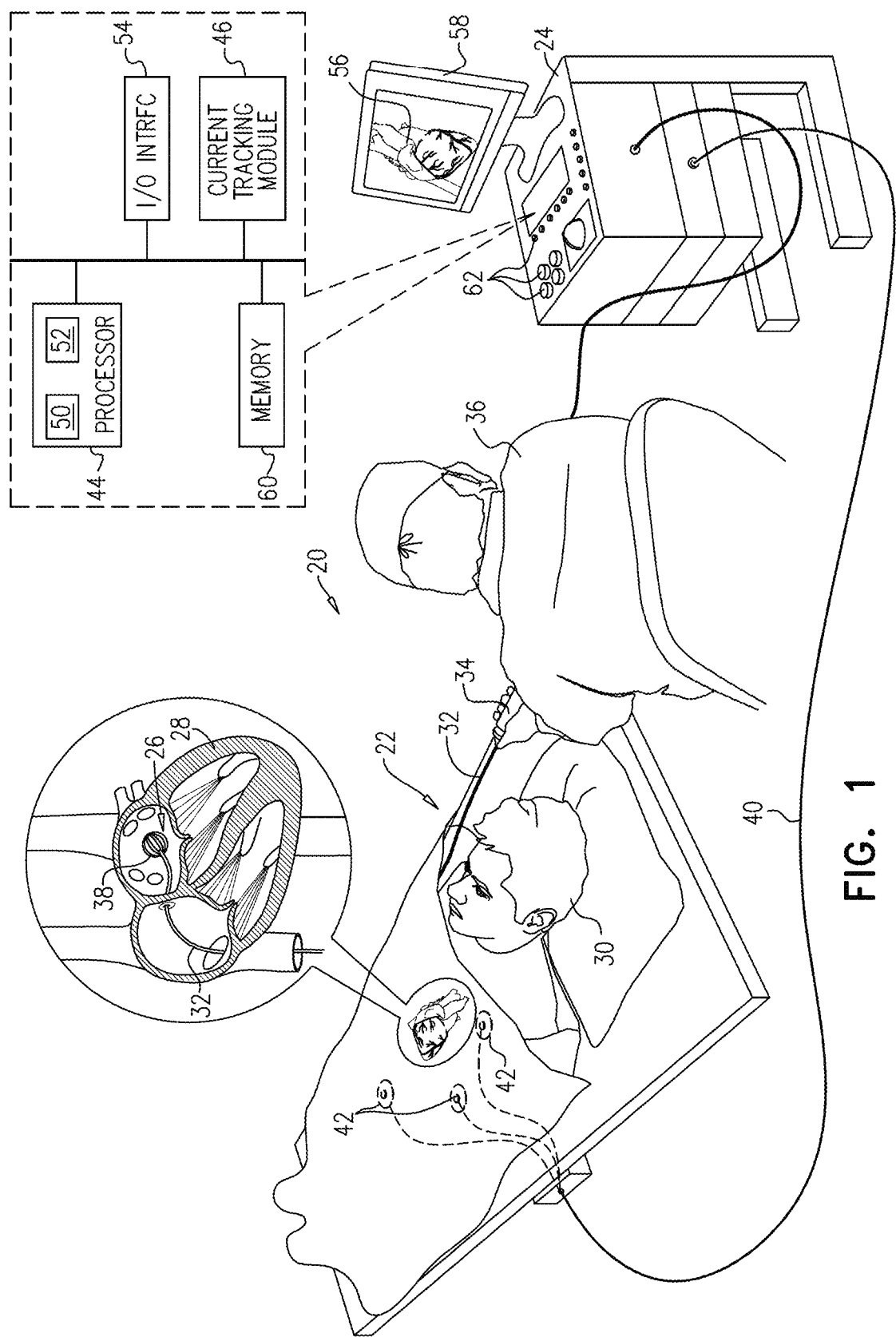
FIG. 1 is a schematic, pictorial illustration of a medical system comprising a basket catheter with a distal end, in accordance with an embodiment of the present invention.

When using a medical probe having multiple electrodes (e.g., basket catheter or a balloon catheter), it may be difficult to accurately position the electrodes with respect to a desired location. For example, during a medical procedure, a medical professional may want to position particular electrodes of a catheter on or close to a focal source of an arrhythmia in myocardial tissue. However, there may be instances during the procedure when the electrodes and/or portions of the tissue are not directly visible to the medical professional. In these instances, even if the electrode locations can be determined, and a camera can be used to view the tissue, it can still be challenging for the medical professional to accurately position the electrodes at the desired locations.

Embodiments of the invention present methods and systems for guiding a distal end of a medical probe toward a treatment location. As described hereinbelow, first and second signals are received from an intracardiac catheter positioned within a heart of a subject and having a distal end comprising a plurality of electrodes. In embodiments of the present invention, the first signals are received from at least three of the electrodes responsive to electrical activity in myocardial tissue with which the at least three of the electrodes are in contact, and the second signals are indicative of respective location coordinates of the at least three electrodes within the heart.

The second signals are processed so as to compute the respective location coordinates of the at least three electrodes, and to determine a geometric center of the respective location coordinates. Based on the first signals and the second signals, an electroanatomical map is generated for an area of the myocardial tissue comprising the determined geometric center, and a focus of an arrhythmia in the area of the myocardial tissue is determined in the map.

To provide positioning guidance to a medical professional, a circle is presented on a display, and within the circle, a region of the map comprising the geometric center and the focus of the arrhythmia is presented so that the geometric center (of the location coordinates of the electrodes) on the map aligns with a center of the circle. In embodiments of the present invention, the region of the map presented within the circle indicates a spatial relationship between the geometric center and the focus of the arrhythmia.

In some embodiments, systems implementing embodiments of the present invention can present the spatial relationship as a circular bulls-eye, where the bulls-eye indicates the location of the focus of the arrhythmia relative to the electrodes. The location of the bulls-eye in the circle can be used to verify that electrodes are close to, or are contacting a desired region. If the electrodes are close to (but not in contact with) the desired region, the medical professional can use the image (e.g., the bulls-eye) as a visual guide for repositioning the distal end of the medical probe in order to move the electrodes to the desired locations.

System Description

Figure 2:
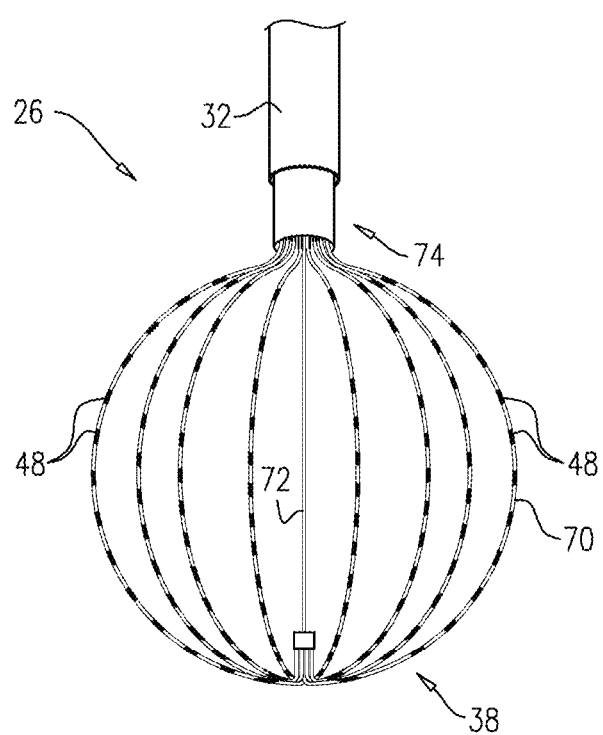
FIG. 2 is a schematic pictorial illustration of the distal end of the basket catheter comprising electrodes affixed to splines of the catheter, in accordance with an embodiment of the present invention.

FIG. 1 is a schematic, pictorial illustration of a medical system 20 comprising medical probe 22 and a control console 24, and FIG. 2 is a schematic pictorial illustration of a distal end 26 of the medical probe, in accordance with an embodiment of the present invention. Medical system 20 may be based, for example, on the CARTO® system, produced by Biosense Webster Inc. of 33 Technology Drive, Irvine, CA 92618 USA. In embodiments described hereinbelow, medical probe 22 can be used for diagnostic or therapeutic treatment, such as for mapping electrical potentials in a heart 28 of a patient 30 (also referred to herein as a subject). Alternatively, medical probe 22 may be used, mutatis mutandis, for other therapeutic and/or diagnostic purposes in the heart or in other body organs.

Probe 22 comprises an insertion tube 32 and a handle 34 coupled to a proximal end of the insertion tube. During a medical procedure, a medical professional 36 can insert probe 22 through the vascular system of patient 30 so that distal end 26 of the medical probe enters a chamber of heart 28. Upon distal end 26 entering the chamber of heart 28, medical professional 36 can deploy an electrode assembly 38 affixed to distal end 26, and the medical professional can manipulate handle 34 to position splines of the electrode assembly so that electrodes on the splines engage myocardial tissue at a desired location or locations. In embodiments of the present invention, electrode assembly 38 may comprise a basket-shaped electrode assembly (as described in the description referencing FIG. 2 hereinbelow) affixed to a basket catheter or a balloon electrode assembly affixed to a balloon catheter.

In the configuration shown in FIG. 1, control console 24 is connected, by a cable 40, to body surface electrodes, which typically comprise adhesive skin patches 42 that are affixed to patient 30. Control console 24 comprises a processor 44 that, in conjunction with a current tracking module 46, determines location coordinates of distal end 26 inside heart 28 based on impedances and/or currents measured between adhesive skin patches 42 and electrodes 48 (FIG. 2) that are affixed to splines of electrode assembly 38. In addition to being used as location sensors during a medical procedure, electrodes 48 may perform other tasks such as measuring electrical activity of heart 28.

As described hereinabove, in conjunction with current tracking module 46, processor 44 may determine location coordinates of distal end 26 inside heart 28 based on impedances and/or currents measured between adhesive skin patches 42 and electrodes 48. Such a determination is typically after a calibration process relating the impedances or currents to known locations of the distal end has been performed. In embodiments of the present invention, electrodes 48 can also be configured to apply a signal to tissue in heart 28, and/or to measure a certain physiological property (e.g., the local surface electrical potential) at a location in the heart.

Processor 44 may comprise real-time noise reduction circuitry 50 typically configured as a field programmable gate array (FPGA), followed by an analog-to-digital (A/D) signal conversion integrated circuit 52. The processor can pass the signal from A/D circuit 52 to another processor and/or can be programmed to determine the location coordinates referred to above.

Although the medical system shown in FIG. 1 uses impedance or current-based sensing to measure a location of distal end 26, other location tracking techniques may be used (e.g., techniques using magnetic-based sensors). Impedance and current-based location tracking techniques are described, for example, in U.S. Pat. Nos. 5,983,126, 6,456,864 and 5,944,022. The methods of location sensing described hereinabove are implemented in the above-mentioned CARTO® system and are described in detail in the patents cited above.

Control console 24 also comprises an input/output (I/O) communications interface 54 that enables the control console to transfer signals from, and/or transfer signals to electrodes 48 and adhesive skin patches 42. Based on signals received from electrodes 48 and/or adhesive skin patches 42, processor 44 can generate an electroanatomical map 56 that shows the location of distal end 26 in the patient's body. During the procedure, processor 44 can present map 56 to medical professional 36 on a display 58, and store data representing the electroanatomical map in a memory 60. Memory 60 may comprise any suitable volatile and/or non-volatile memory, such as random access memory or a hard disk drive. In some embodiments, medical professional 36 can manipulate map 56 using one or more input devices 62. In alternative embodiments, display 58 may comprise a touchscreen that can be configured to accept inputs from medical professional 36, in addition to presenting map 56.

In the example shown in FIG. 2, electrode assembly 38 is configured as a basket-shaped electrode assembly that has a plurality of splines 70 connected at their proximal and distal ends. Basket-shaped electrode assembly 38 has an expanded arrangement wherein splines 70 bow radially outwardly and a collapsed arrangement wherein the splines are arranged generally along the axis of insertion tube 32. In some embodiments, the distance between the proximal and distal ends of basket-shaped electrode assembly 38 may be shortened, such as by moving puller wire 72 proximally, causing splines 70 to bow outwards into the expanded configuration. During a medical procedure, basket-shaped electrode assembly 38 can assume an expanded configuration when unconstrained, such as by being advanced out of a lumen 74 at distal end 26.

Each given spline 70 comprises one or more electrodes 48. In addition to using electrodes 48 to determine the location of basket-shaped electrode assembly 38, the electrodes can also be used to measure a physiological property such as local surface electrical potentials at respective locations on myocardial tissue 110. In additional embodiments, electrodes 48 can be configured to deliver ablation power (e.g., radio-frequency energy) to the myocardial tissue.

Figure 3:
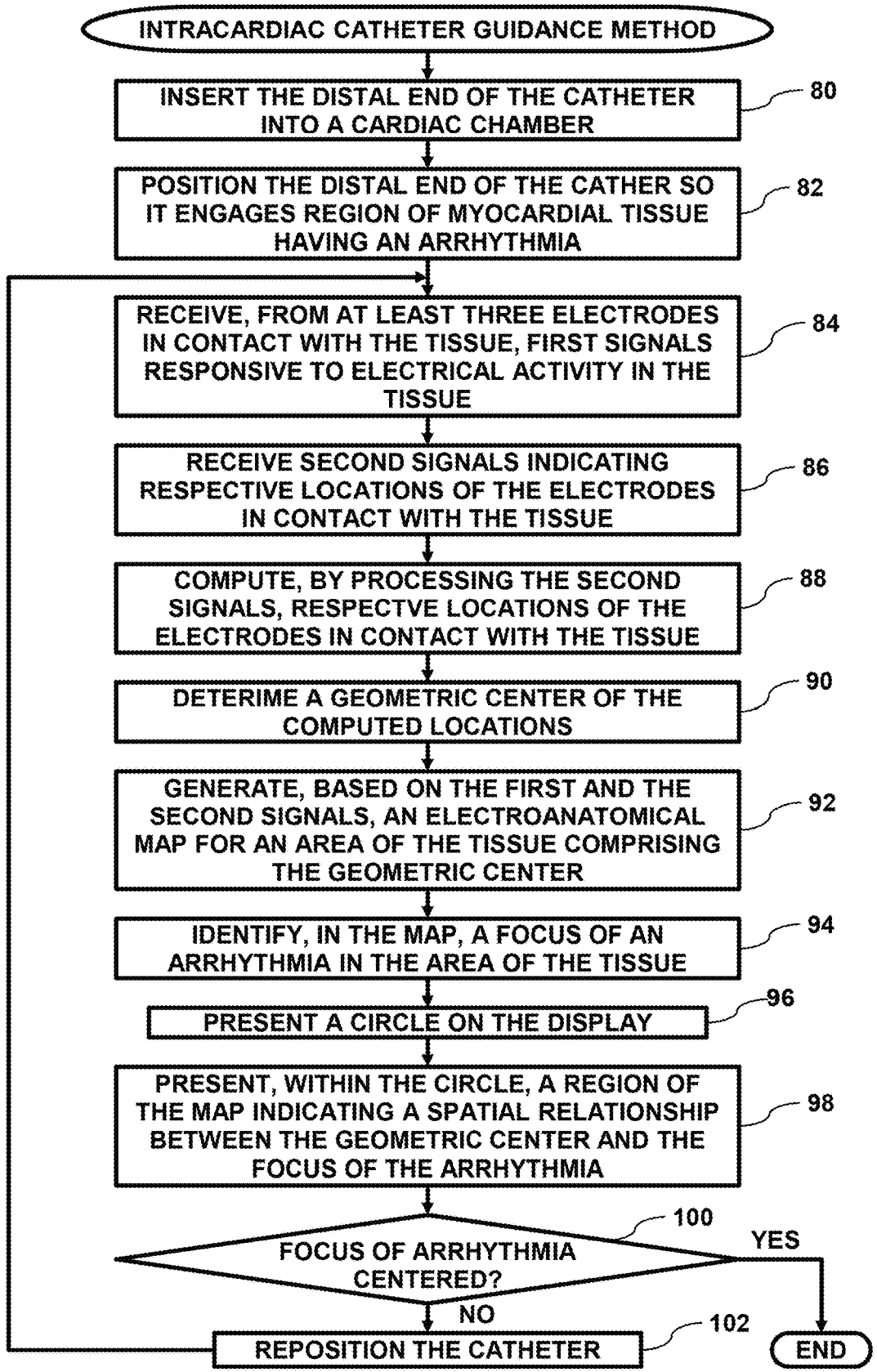
FIG. 3 is a flow diagram that schematically illustrates a method of providing, to medical professional, visual feedback for guiding the distal end of the balloon catheter, in accordance with an embodiment of the present invention.
Figure 4:
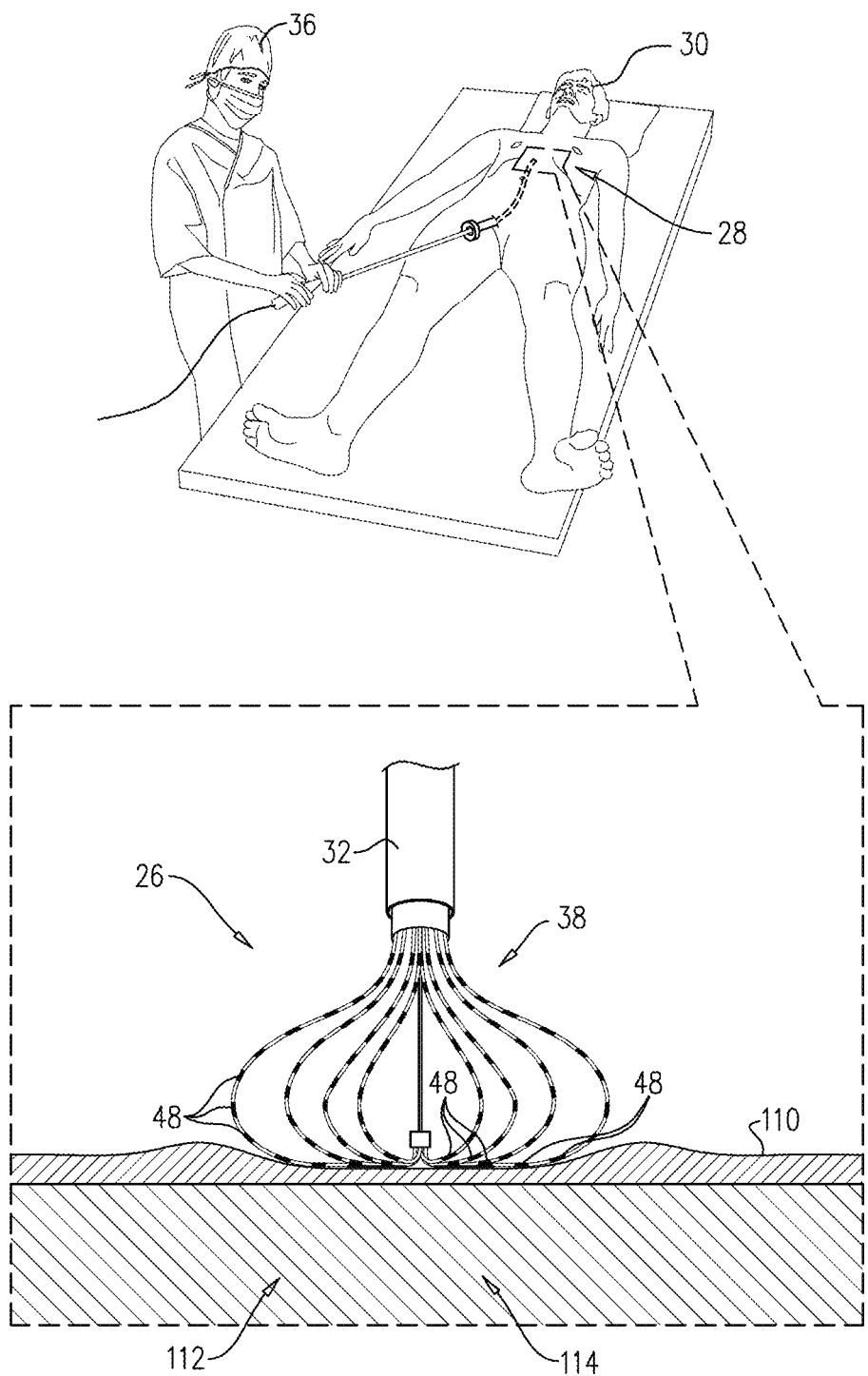
FIG. 4 is a schematic pictorial illustration of the electrodes engaging myocardial tissue in a heart during a medical procedure, in accordance with an embodiment of the present invention.

FIG. 3 is a flow diagram that schematically illustrates a method of providing, to medical professional 36, visual feedback for guiding electrode assembly 38 in heart 28, and FIG. 4 is a schematic pictorial illustration of electrodes 48 engaging myocardial tissue 110 in the heart during a medical procedure, in accordance with an embodiment of the present invention. While the steps of the flow diagram are described using medical probe 22 comprising electrodes 48 mounted on basket-shaped electrode assembly 38, using any other type of medical probe, e.g., a balloon catheter, that comprises multiple electrodes that can simultaneously measure physiological properties at respective locations on myocardial tissue 110 are considered to be within the spirit and scope of the present invention.

In an insertion step 80, medical professional 36 inserts distal end 26 of medical probe 22 into a chamber of heart 28. Upon inserting distal end 26 into the chamber, medical professional 36 can deploy electrode assembly 38 from lumen.

In a positioning step 82, medical professional 36 manipulates handle 34 so that electrodes 48 at distal end 26 engages a region 112 on myocardial tissue 110 having an arrhythmia.

In a first receive step 84, processor 44 receives, from at least three electrodes 48, first signals responsive to electrical activity in the myocardial tissue engaged by the electrodes. In some embodiments, the electrical activity indicates local activation times in the myocardial tissue.

In a second receive step 86, the processor receives second signals indicating respective locations of the electrodes engaging the myocardial tissue. In the configuration shown in FIG. 1, processor 44 receives the second signals from the body surface electrodes in adhesive skin patches 42 in response to electrical currents conveyed by the processor to electrodes 48.

In a computation step 88, processor 44 processes the received second signals to compute respective locations of the electrodes engaging myocardial tissue 110, and in a determination step 90, the processor determines, on the myocardial tissue, a geometric center 114 of the computed locations.

In a generation step 92, processor 44 generates, for region 112, electroanatomical map 56 based on the received first and second signals, and in an identification step 94, the processor identifies, in the electroanatomical map, a focus of an arrhythmia. Arrythmias may be identified using local activation times (LATs) of the myocardial tissue, and the processor may identify the focus of a particular arrhythmia using LATs of the tissue. For example, the processor may identify the focus of a focal arrhythmia as being a region of the arrhythmic tissue having the lowest LAT; and may identify the focus of a rotor as being the region of the arrhythmic tissue about which the LAT values rotate. Implementation of the present embodiment using other methods for processor 44 to identify the focus of an arrhythmia are also considered to be comprised within the scope of the present invention.

In a first presentation step 96, processor 44 presents a circle on display 58, and in a second presentation step 98, the processor presents, within the circle, a region of the electroanatomical map comprising the geometric center and the focus of the arrhythmia so that the geometric center on the electroanatomical map aligns with a center of the circle.

As presented in FIGS. 5-9 which are described hereinbelow, the region of the electroanatomical map presented within the circle indicates a spatial relationship between the geometric center and the focus of the arrhythmia. In some embodiments, processor 44 can present the spatial relationship by plotting local activation time values against their respective locations.

Figure 5:
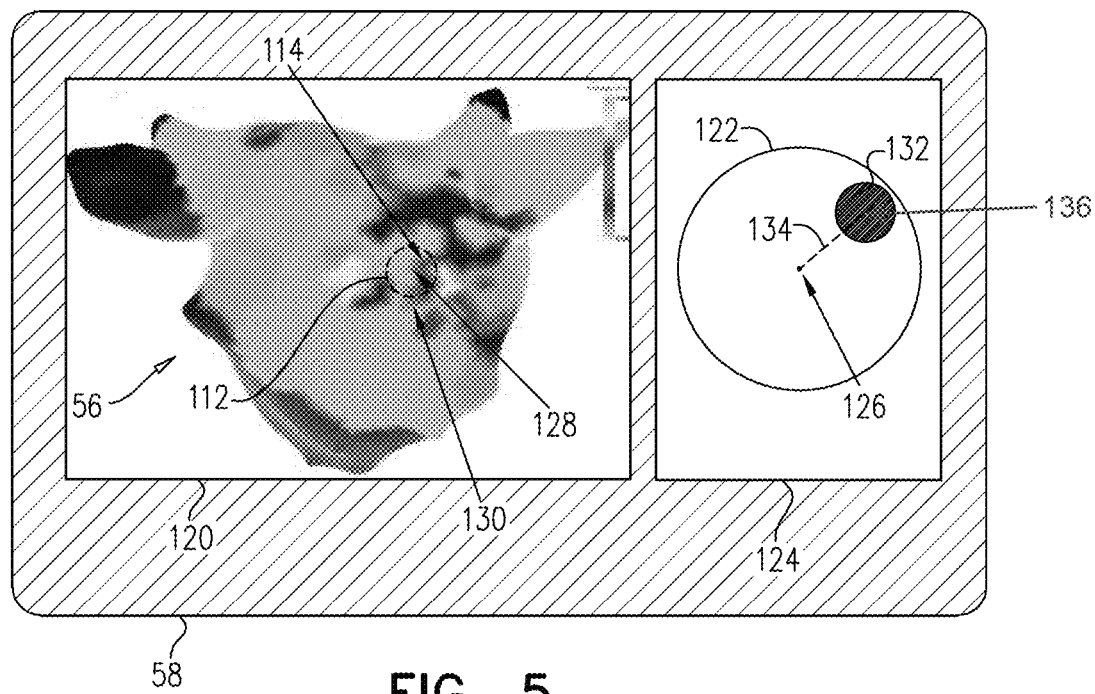
FIG. 5 is a schematic pictorial illustration of presenting an electroanatomical map on a display, in accordance with a first embodiment of the present invention.

FIG. 5 is a schematic pictorial illustration of electroanatomical map 56 presented on display 58, in accordance with a first embodiment of the present invention. In the first embodiment of the present invention, processor 44 presents, on display 58, electroanatomical map 56 in a first window 120, and a circle 122 in a second window 124. Circle 122 corresponds to a region of electroanatomical map 56 so that a center 126 of circle 122 aligns with a geometric center 128 of an arrhythmia 130. In some embodiments, processor 44 can present a visual indicator 132 (e.g., an icon) that corresponds to a location of a focus 136 of arrhythmia and indicates a spatial relationship between geometric center 128 and the focus of the arrhythmia. In embodiments of the present invention, processor 44 can present the spatial relationship as a "bulls-eye" that indicates a distance 134 between visual indicator 132 (that corresponds to focus 136) and circle center 126 (that corresponds to geometric center 128).

In embodiments of the present invention, processor 44 can present map 56 at a first resolution, and present circle 122 comprising the region on the myocardial tissue having the arrhythmia at a second resolution greater than the first resolution. Presenting the region on the myocardial tissue having the arrhythmia at a higher resolution (and therefore presenting the region having the arrhythmia in more detail) can assist medical professional 36 in positioning electrodes 48 at appropriate locations for treating arrhythmia 130.

Figure 6:
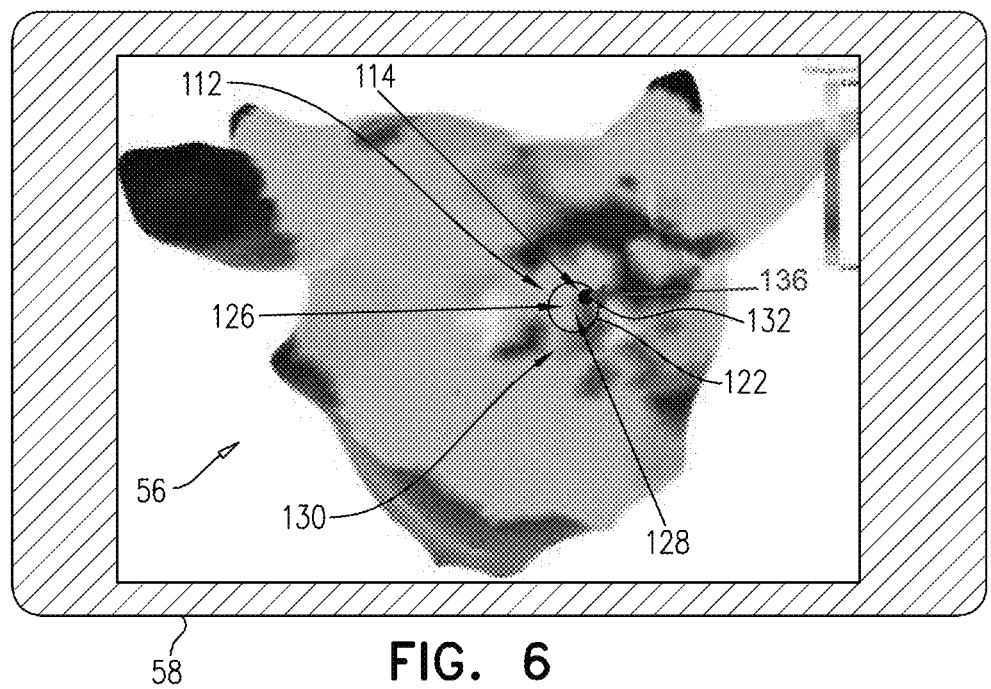
FIG. 6 is a schematic pictorial illustration of presenting the electroanatomical map on the display, in accordance with a second embodiment of the present invention.

FIG. 6 is a schematic pictorial illustration of electroanatomical map 56 presented on display 58, in accordance with a second embodiment of the present invention. In the second embodiment of the present invention, processor 44 presents, on display 58, electroanatomical map 56, and overlays circle 122 and visual indicator 132 on the electroanatomical map 56 so that circle center 126 aligns with geometric center 128 and visual indicator 132 aligns with arrhythmia focus 136.

In a third embodiment, processor 44 can combine the first and second embodiments described supra by presenting circle 122 and visual indicator 132 in window 124, presenting electroanatomical map 56 in window 120, and overlaying the circle and the visual indicator on the electroanatomical map.

In the examples presented in FIG. 5 (and in FIGS. 6-9), geometric center 128 is in close proximity to focus 136, and processor 44 presents visual indicator 132 within circle 122. However, if geometric center 128 is not in close proximity to focus 136, processor 44 can presents visual indicator 132 outside circle 122.

Returning to the flow diagram, in a decision step 100, if medical professional 36 observes that the focus of the ablation is not centered in the circle (e.g., as shown in FIGS. 5, 6, 7A, 8A and 9A), then the medical professional repositions distal end 26 in a repositioning step 102, and the method continues with step 84. If medical professional 36 observes that the focus of the ablation is centered in the circle (e.g., as shown in FIGS. 7B, 8B and 9B), then the method ends. In some instances, medical professional can instruct control console 24 to deliver ablation power (e.g., radio-frequency energy) to electrodes 48 in order to ablate the region of myocardial tissue comprising the arrhythmia.

Figure 7A:
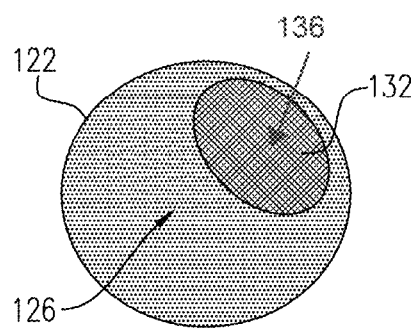
FIGS. 7A and 7B are schematic pictorial illustrations of visual indicators that can be presented on the display to help a medical professional position the distal end of the medical probe at an area of tissue requiring treatment, in accordance with embodiments of the present invention.
Figure 7B:
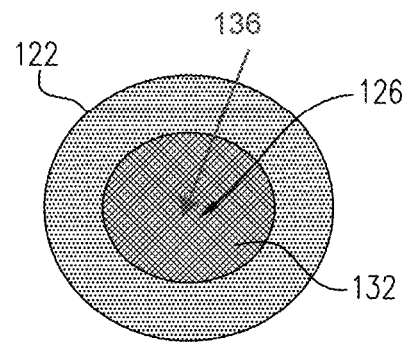

FIGS. 7A and 7B, also referred to herein collectively as FIG. 7, are schematic pictorial illustrations of circle 122 and visual indicator 132 for arrhythmia 130 comprising a focal arrhythmia, in accordance with an embodiment of the present invention. In FIG. 7A, visual indicator 132 is not aligned with circle center 126, thereby indicating that geometric center 128 is not aligned with focus 136. In FIG. 7B, visual indicator 132 is aligned with (i.e., overlaps) circle center 126, thereby indicating that geometric center 128 is aligned with focus 136.

Figure 8A:
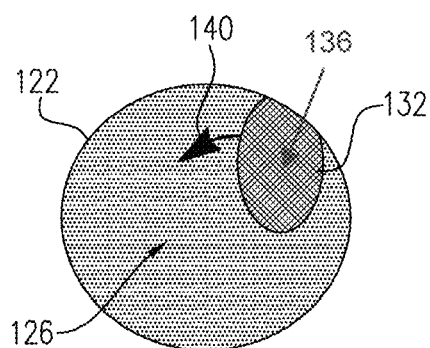
FIGS. 8A and 8B are schematic pictorial illustrations of circle and visual indicator for arrhythmia comprising a rotor arrhythmia having a single focus.
Figure 8B:
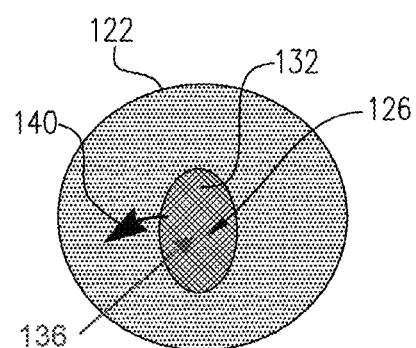

FIGS. 8A and 8B, also referred to herein collectively as FIG. 8, are schematic pictorial illustrations of circle 122 and visual indicator 132 for arrhythmia 130 comprising a rotor arrhythmia having a single focus 136, in accordance with an embodiment of the present invention. In the example presented in FIGS. 8A and 8B, an arrow 140 indicates a path of the arrhythmia from focus 136 in myocardial tissue 110. In FIG. 8A, visual indicator 132 is not aligned with circle center 126, thereby indicating that geometric center 128 is not aligned with focus 136. In FIG. 8B, visual indicator 132 is aligned with (i.e., overlaps) circle center 126, thereby indicating that geometric center 128 is aligned with focus 136.

Figure 9A:
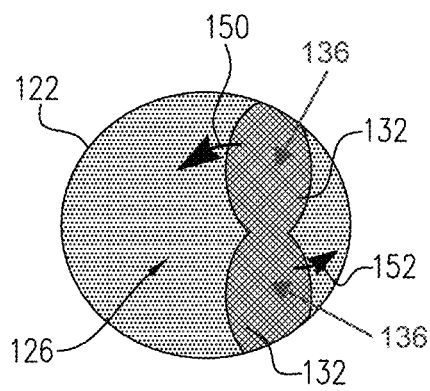
FIGS. 9A and 9B are schematic pictorial illustrations of circle and visual indicator for arrhythmia comprising a rotor arrhythmia having two focuses.
Figure 9B:
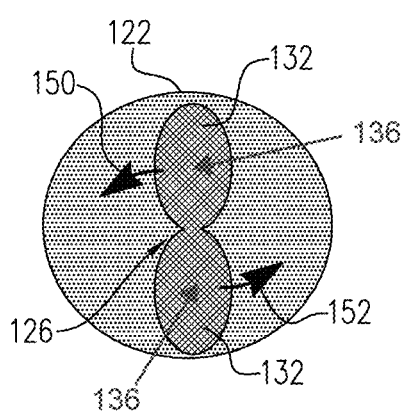

FIGS. 9A and 9B, also referred to herein collectively as FIG. 9, are schematic pictorial illustrations of circle 122 and visual indicator 132 for arrhythmia 130 comprising a rotor arrhythmia having two focuses 136, in accordance with an embodiment of the present invention. In the example presented in FIGS. 9A and 9B, arrows 150 and 152 indicate paths of the arrhythmias from their respective focuses 136 in myocardial tissue 110. In FIG. 9A, visual indicator 132 is not aligned with circle center 126, thereby indicating that geometric center 128 is not aligned with focus 136. In FIG. 9B, visual indicator 132 is aligned with (i.e., overlaps) circle center 126, thereby indicating that geometric center 128 is aligned with focus 136.

While the description referencing FIGS. 5, 6, 7A, 7B, 8A, 8B and 9A and 9B describe processor 44 presenting circle 122 on display 58, presenting any type of ovular shape corresponding to a region of map 56 is considered to be within the spirit and scope of the present invention.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical system comprising:
   a tubular shaft having a proximal end and a distal end, the tubular shaft extending along a longitudinal axis;
   an expandable basket assembly coupled to the distal end of the tubular shaft, the expandable basket assembly comprising:
      a plurality of splines configured to bow radially outward from the longitudinal axis; and
      a plurality of electrodes attached to the plurality of splines;
   a processor; and
   a memory in communication with the processor and storing instructions configured to cause the system to:
      receive a first signal indicative of electrical activity in myocardial tissue, the first signal being received from the plurality of electrodes of the expandable basket assembly;
      receive a second signal indicative of a respective position of the plurality of electrodes of the expandable basket assembly;
      determine a geometric center of the plurality of electrodes of the expandable basket assembly;
      determine a focus of an arrhythmia in the myocardial tissue;
      output, to a display, a geometric shape corresponding to an area proximate the geometric center;
      output, to the display, a region indicative of the focus of the arrhythmia; and
      output, to the display, an indication of a spatial relationship between the geometric center and the focus of the arrhythmia.

2. The medical system of claim 1, wherein the instructions are further configured to cause the system to:
   generate an anatomical map indicative of the electrical activity of the myocardial tissue; and
   output, to the display, the anatomical map.

3. The medical system of claim 2, wherein the instructions are further configured to cause the system to output, to the display, an overlay of the geometric shape and the region and the anatomical map.

4. The medical system of claim 1, the plurality of electrodes comprising at least three electrodes.

5. The medical system of claim 1, wherein the electrical activity comprises local activation time values.

6. The medical system of claim 5, wherein outputting, to the display, the region indicative of the focus of the arrhythmia comprises plotting the local activation time values against their respective locations.

7. The medical system of claim 1, wherein the geometric shape comprises a circle and the indication of the spatial relationship between the geometric center and the focus of the arrhythmia comprises displaying the region within the circle.

8. The medical system of claim 1 further comprising outputting, to the display, a path of the arrhythmia from the focus of the arrhythmia.

9. The medical system of claim 1, wherein the region is indicative of the arrhythmia comprising more than one focus.

10. The medical system of claim 1, wherein the plurality of electrodes are configured to deliver ablation energy to the myocardial tissue.

11. The medical system of claim 1, wherein the second signal is received from a body surface electrode applied to a body surface.

12. A method, comprising:
   receiving, from a plurality of electrodes disposed on a distal end of a catheter, a first signal indicative of electrical activity in myocardial tissue, the catheter comprising an expandable basket assembly coupled to the distal end of the catheter, the expandable basket assembly comprising a plurality of splines configured to bow radially outward from a longitudinal axis and the plurality of electrodes attached to the plurality of splines;
   receiving a second signal indicative of a respective position of the plurality of electrodes of the expandable basket assembly;
   determining a geometric center of the plurality of electrodes of the expandable basket assembly;
   determining a focus of an arrhythmia in the myocardial tissue;
   outputting, to a display, a geometric shape corresponding to an area proximate the geometric center;
   outputting, to the display, a region indicative of the focus of the arrhythmia; and
   outputting, to the display, an indication of a spatial relationship between the geometric center and the focus of the arrhythmia.

13. The method of claim 12, the plurality of electrodes comprising at least three electrodes.

14. The method of claim 13, wherein the electrical activity comprises local activation time values.

15. The method of claim 14, wherein outputting, to the display, the region indicative of the focus of the arrhythmia comprises plotting the local activation time values against their respective locations.

16. The method of claim 15 further comprising:
    generating an anatomical map indicative of the electrical activity of the myocardial tissue; and
    outputting, to the display, the anatomical map.

17. The method of claim 16 further comprising outputting, to the display, an overlay of the geometric shape and the region and the anatomical map.

18. The method of claim 17, wherein the second signal is received from the catheter.

19. The method of claim 17, wherein the second signal is received from a body surface electrode applied to a body surface.

* * * * *